United States Patent

Buchin et al.

[11] 3,978,082
[45] Aug. 31, 1976

[54] DERIVATIVES OF DINITRO-2,2'-BITHIOPHENE AND APPLICATION THEREOF

[76] Inventors: Petr Ivanovich Buchin, ulitsa Krasnoarmeiskaya, 23, kv. 80; Adolf Evgenievich Lipkin, ulitsa Nevskaya, 5, kv. 51, both of Kuibyshev; Ernest Alexandrovich Rudzit, Noginsky raion, poselok Staraya Kupavna, mikroraion dom 5, kv. 24, Moskovskaya oblast; Boris Alexeevich Zenin, prospekt Lenina, 16, kv. 134, Kuibyshev; Maxim Georgievich Viderker, ulitsa Fadeeva, 67, kv. 45, Kuibyshev; Viktor Alexandrovich Smirnov, Partizanskaya ulitsa, 148, kv. 42, Kuibyshev; Irina Petrovna Balmasova, prospekt Kirova, 258, kv. 45, Kuibyshev; Evgeny Vladimirovich Orlov, ulitsa Vilonovskaya, 2a, kv. 8, Kuibyshev; Larisa Alexandrovna Chichkova, ulitsa Novo-Sadovaya, 42, kv. 616, Kuibyshev, all of U.S.S.R.

[22] Filed: Dec. 23, 1974

[21] Appl. No.: 535,849

[52] U.S. Cl............................. 260/329 HS; 424/275; 260/332.3 R
[51] Int. Cl.²...................................... C07D 333/00
[58] Field of Search.............................. 260/329 HS

[56] References Cited
OTHER PUBLICATIONS
Carpanelli et al., Chem. Abst., vol. 56 (1952) p. 7251e.

*Primary Examiner*—James O. Thomas, Jr.
*Assistant Examiner*—A. Siegel
*Attorney, Agent, or Firm*—Haseltine, Lake & Waters

[57] ABSTRACT

The novel compounds, viz. derivatives of dinitro-2,2'-bithiophenes of the structural formula

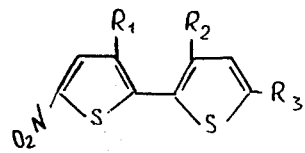

where
$R_1 = NO_2$, if $R_2 = H$;
$R_3$ is a formyl group, a ketone group or an azomethine group;
$R_1 = H$, if $R_2 = NO_2$;
$R_3$ is a formyl group, a ketone group or an azomethine group.

The novel chemotherapeutic preparation for treating human dermatophytoses comprises an active ingredient, viz. -5',3'-dinitro-5-acetyl-2,2'-bithiophene having the following structural formula

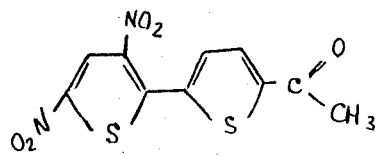

combined with a pharmaceutical carrier.

5 Claims, No Drawings

DERIVATIVES OF DINITRO-2,2'-BITHIOPHENE AND APPLICATION THEREOF

The present invention relates to novel compounds, viz. derivatives of dinitro-2,2'-bithiophene, and to the application thereof.

In accordance with the invention, the novel derivatives of dinitro-2,2'-bithiophene have the following structural formula

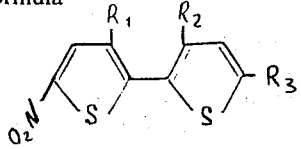

where
$R_1 = NO_2$, if $R_2 = H$;
$R_3$ is a formyl group, a ketone group or an azomethyne group;
$R_1 = H$, if $R_2 = NO_2$;
$R_3$ = a formyl group, a ketone group or an azomethine group.

Said derivatives of dinitro-2,2'-bithiophene are bitter, odorless, predominantly yellow crystalline substances, practically insoluble in water, extremely scantily soluble in alcohol, difficulty soluble in vegetable oils, soluble in chloroform, readily soluble in dimethylformamide and dimethylsulfoxide, and sensitive to direct sunlight.

Said compounds exhibit pharmacological activity and find application in medicine as antimycotics.

The substances of this group are distinguished by virtue of their pronounced selective fungicidal activity, particularly as far as dermatomycetes are concerned. For this reason they are employed for chemotherapy of human dermatophytoses (epidermophytosis, trichophytosis, microsporia and oidiomycosis).

For two isomers of dinitrobithiophene aldehyde, viz. 5',3'-dinitro-5-formyl-2,2'-bithiophene and 5',3-dinitro-5-formyl-2,2'-bithiophene, the fungicidal dose in regard to dermatomycetes is from 2 to 5 micrograms per milliliter; for dinitrobithiophene methyl ketone, an isomer of 5',3'-dinitro-5-acetyl-2,2'-bithiophene, it is from 1 to 3 mcg/ml; for dinitrobithiophene azomethines, e.g. N-(5',3'-dinitro-2,2'-dithienylidene-5)-meta-aminobenzoic acid, the fungicidal dose is from 3 to 5 mcg/ml. Although the level of fungicidal activity of dinitrobithiophene methyl ketone and dinitrobithiophene aldehyde is the same, the latter compound is less important in terms of its medical value.

The reason for this should be sought in the fact that dinitrobithiophene aldehyde is more toxic for animal organisms (administered intraperitoneally to white mice, its $LD_{50}$ is 45 mg/kg) and has a strong irritating effect when applied onto the skin of animals and humans, particularly in occlusive dressings and as applied to allergic patients.

Chemical compounds obtained on the basis of dinitrobithiophene aldehyde, for instance such a dinitrobithiophene azomethine as N-(2,2'-2,2'-dithienylidene-5)-meta-aminobenzoic acid of the following structural formula

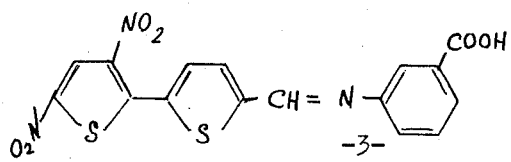

prove to be far less toxic and have a much less pronounced irritating effect than dinitrobithiophene aldehyde proper.

The former derivative of dinitrobithiophene aldehyde is a highly active antimycotic agent, superior in activity to such widely known antimycotics as Nitrofungin (Czechoslovakia, "SPOFA" CO.) or undecylenic acid. Its fungistatic dose as titrated in vitro on solid and liquid Saburo media in respect of dermatomycetes is 1 to 3 mcg/ml and its fungicidal dose is from 3 to 5 mcg/ml; the anticandida fungistatic and fungicidal dose is 6 mcg/ml.

Its bactericidal dose for Gram-positive bacteria which are more sensitive to this compound than other bacterial species, inter alia, for Staphylococcus aureus, is 25 mcg/ml.

N-(5',3'-dinitro-2,2'-dithienylidene-5)-meta-aminobenzoic acid is not classified with highly toxic substances (administered intraperitoneally to white mice, its $LD_{50}$ is 100 mg/kg).

This substance has a mild irritating effect on eye tissues administered as an ointment composed of 0.1 g of the substance in question, 2 ml of dimethylsulfoxide and 8 g of lanolin (1-percent ointment); but it has no irritating effect on the skin of animals or humans in multiple applications of the ointment of the above composition.

A 1-percent solution of the substance in question in dimethysulfoxide in 11 out of 13 cases effectively prevents experimental mycosis in guinea pigs caused by a virulent strain of Trichophyton gypseum, provided the drug is daily applied onto the infected area once every day for 5 days starting on the third day after infection (all other conditions being equal Nitrofungin prevents the development of experimental mycosis in 7 out of 13 cases).

By the combination of such paramount properties as antimycotic activity in respect of dermatomycetes and harmlessness for animals and human beings, the most valuable substance of this group is dinitrobithiophene methyl ketone whose most active isomer is 5',3'-dinitro-5-acetyl-2,2'-bithiophene having the following empirical and structural formulas:

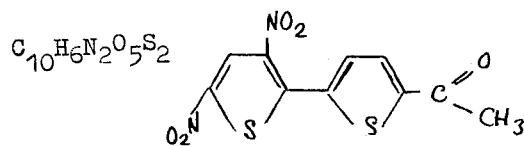

and a molecular weight of 298.29, which is employed as the active ingredient of the proposed medicinal preparation.

In accordance with the invention, the proposed chemotherapeutic antimycotic preparation for treating dermatophytoses comprises an active ingredient, viz. 5',3'-dinitro-5-acetyl-2,2'-bithiophene of the structural formula

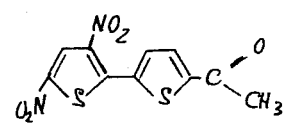

combined with a pharmaceutical carrier.

The active ingredient of the proposed preparation is a yellow, odorless, bitter crystalline powder, practically insoluble in water, very scantily soluble in alcohol, difficultly soluble in sunflower oil (up to 1 percent), soluble in chloroform and easily soluble in dimethylformamide and dimethylsulfoxide, having a melting point of 122° to 122.5°C., absorbing in the UV spectrum at $\lambda'_{max} = 273$ nm $- \epsilon'_{max} = 14.530$ and at $\lambda''_{max} = 375$nm $-\epsilon''_{max} = 14,010$, and absorbing in the IR spectrum at $\nu$ cm$^{-1}$: 1,663, 1,552, 1,515, 1,500, 1,423, 1,390, 1,335, 1,310, 1,263, 1,072, 878, 808, 778 and 724. The substance in question is sensitive to direct sunlight, but is quite stable if stored in a dark-glass vial. Its decomposition temperature is 89°C.

Upon addition of several drops of a saturated alcohol solution of sodium hydroxide to an alcohol solution of the substance in question, the latter is colored dark-red. Such a color test may be successfully employed for indication of said substance in its therapeutic form, as well as in experimental studies of the pathways of its penetration from the therapeutic form into the skin and internal medium of the organism. Using a photoelectrocolorimeter and a special standard scale in such a color test, one can quantitatively evaluate the level of dinitrobithiophene methyl ketone in the substrate.

In vitro titration on solid and liquid Saburo media of the fungistatis and fungicidal doses of said compound in respect of the fungi *Tr. rubrum*, *Tr. interdigitale*, *Microsporon lanosum* and *Tr. gypseum* showed said substance to have a high antimycotic activity in respect of dermatomycetes, exceeding that of such widely known antimycotics as Nitrofungin (Czechoslovakia, SPOFA CO.) and undecylenic acid. Thus, inter alia, for 5′,3′-dinitro-5-acetyl-2,2′-bithiophene the fungistatic dose is 0.5 to 2 mcg/ml and the fungicidal dose is 1 to 3 mcg/kg, whereas for Nitrofungin, whose active ingredient is 2-chloro-4-nitrophenyl, the respective doses are 5 and 5 to 10 mcg/ml and for undecylenic acid the respective doses are 5 to 10 to 20 and 5 to 20 to 50 mcg/ml. The fungicidal activity of 5′,3′-dinitro-5-acetyl-2,2′-bithiophene in biological media declines insignificantly (by not more than 20 percent).

Said compound also has a fungicidal effect on oidiomycetes, namely *Candida albicans*, the level of its activity in respect of the latter fungi likewise being higher than those of Nitrofungin and undecylenic acid. Thus, the anticandida fungicidal dose for 5′,3′-dinitro-5-acetyl-2,2′-bithiophene is 2 to 5 to 10 mcg/ml, whereas for Nitrofungin it is 20 mcg/ml and for undecylenic acid 20 to 50 mcg/ml.

The antibacterial activity of 5′,3′-dinitro-5-acetyl-2,2′-bithiophene in vitro is low. Thus, for instance, the bactericidal dose of 5′,3′-dinitro-5-acetyl-2,2′-bithiophene for *Staphylococcus aureus*, the most sensitive of all bacteria to this substance, is 15 to 35 mcg/ml (the staphylocidal dose of Nitrofungin is 150 mcg/ml, that of undecylenic acid 350 mcg/ml). The low bactericidal activity of said substance emphatically shows the selective pattern of its fungicidal effect.

Said substance is not classified with highly toxic agents. Administered per os to white mice in the form of oil solutions, the LD$_{50}$ of 5′,3′-dinitro-5-acetyl-2,2′-bithiophene is 446 mg/kg; administered subcutaneously 500 mg/kg; and administered intraperitoneally 213 mg/kg.

Rabbits weighing 2.5 to 3 kg are not affected whatsoever by 5-ml subcutaneous injections of a 1-percent oil (sunflower oil) solution of 5′,3′-dinitro-5-acetyl-2,2′-bithiophene. Similar 10-ml injections are likewise innocuous for dogs weighing 10 to 12 kg. In the form of a 1-percent oil solution, said substance has no irritating effect both when applied onto the skin of animals and humans and when instilled in the eyes of rabbits for 5 days once a day.

Since 5′,3′-dinitro-5-acetyl-2,2′-bithiophene is a highly active antimycotic, its logical field of application is chemotherapy of human dermatophytoses, said substance being prescribed for external application in the form of predominantly oil solutions or ointments, the latter being a preferred medicinal form.

In accordance with the invention, a preferred pharmaceutical carrier of the proposed chemotherapeutic antimycotic preparation is an ointment base composed of a vegetable oil and anhydrous lanolin taken in a 1:1 ratio. The proposed medicinal preparation preferably comprises 0.5 percent by weight of the active ingredient.

The recommended antimycotic ointment has the following composition:
active ingredient, 0.5 g
vegetable oil, 50 g
anhydrous lanolin, up to 100 g.

In order to prepare an ointment of the above composition, an aliquot of 5′,3′-dinitro-5-acetyl-2,2′-bithiophene is dissolved as completely as possible in an appropriate quantity of e.g. sunflower oil with continuous stirring and heating in a hot-water bath to a temperature of not higher than 80°C., after which an appropriate quantity of molten lanolin is added with continuous stirring to produce a homogeneous mass which is poured into dark-glass vials with covers and allowed to solidify at ambient temperature. The vials must be kept in a cool and dark place.

The above-described 0.5-percent ointment of the proposed preparation is a homogeneously dense, yellow-brown, bitter substance devoid of any specific odor.

Prolonged (45 days) daily cutaneous applications of the above 0.5-percent ointment of 5′,3′-dinitro-5-acetyl-2,2′-bithiophene to guinea pigs and rabbits were not accompanied by any toxic phenomena, loss of weight, alterations of the blood picture, or disturbances of the animals' state and behavior. That said ointment had no toxic effect on the animals' organisms was corroborated by histological findings.

The mild effect of the ointment is attributable to the poor ability of the active ingredient to penetrate via the skin into the internal media of the organism. Thus, the above-described color test failed to detect 5′,3′-dinitro-5-acetyl-2,2′-bithiophene in the blood, urine and extracts from the internals of experimental animals (guinea pigs and rabbits) previously subjected to prolonged cutaneous applications of the 0.5-percent ointment of the above composition.

5′,3′-dinitro-5-acetyl-2,2′-bithiophene is invariably found by the color test in the skin of animals after multiple cutaneous applications of the 0.5-percent ointment of the above composition, testifying to a comparatively high penetrability of the active ingredient. Thus, for instance, after 1 month and one half of cutaneous applications of the ointment, the level of 5′,3′-dinitro-5-acetyl-2,2′-bithiophene in the skin of guinea pigs and rabbits was quantitatively evaluated at 3.24 to 5.27 mcg/sq.cm. with the aid of photoelectrocolorimetry using a standard scale. Moreover, the active principle persists in the skin long after the medicinal form applications have been discontinued (traces of 5',3'-dinitro-5-acetyl-2,2'-bithiophene are detected in the skin by means of the color test as late as 10 to 14 days after the last application).

Experiments with the use of human cadaver skin showed that a mere 24 hours after the application of 5',3'-dinitro-5-acetyl-2,2'-bithiophene in the form of a 0.5-percent ointment the active ingredient penetrated the skin to the extent of 0.3 percent of the dose applied. The color test also revealed the ability of 5',3'-dinitro-5-acetyl-2,2'-bithiophene to penetrate the hair.

The high skin penetrability of the active ingredient of this invention combined with its capacity for accumulation and lengthy preservation in skin tissues cannot but affect the state of these tissues. As shown by histological studies of the skin of guinea pigs from areas long exposed to applications of a 0.5-percent ointment of the proposed preparation, certain reactive alterations do occur in the skin epidermis caused by 5',3'-dinitro-5-acetyl-2,2'-bithiophene, namely manifestations of hyperkeratosis and some thinning of the Malpighian layer, but these alterations are not destructive.

Chemotherapy of experimental mycosis of guinea pigs, induced by a virulent strain of *Trichophyton gypseum*, the most resistant to the preparation, confirmed that 5',3'-dinitro-5-acetyl-2,2'-bithiophene retained its antimycotic properties in vivo. Daily application of a 0.5-percent ointment of 5',3'-dinitro-5-acetyl-2,2'-bithiophene onto the infected areas once a day for 25 days produced a cure of the animals within a shorter period of time as compared with the effect of Nitrofungin.

While planning the application of 5',3'-dinitro-5-acetyl-2,2'-bithiophene, one should take into account, along with its direct fungicidal effect, also such factors as its high penetrability into the skin and hair afflicted by the fungus, its ability to be retained by the skin for a long period of time, and finally its lack of immunodepressive effect. The latter fact was determined by comparative evaluation of the immunological indices in a group of animals with experimental mycosis some of which were treated with a 0.5-percent ointment of the preparation while the others were not.

The results of clinical trials of the 0.5-percent ointment of 5',3'-dinitro-5-acetyl-2,2'-bithiophene give good grounds to assert that the proposed preparation is a highly effective chemotherapeutic aglut for many forms of dermatophytosis, including infiltratively suppurative trichophytosis, microsporia, inguinal epidermophytosis, rubrophytosis of the smooth skin and nails, as well as candidosis of the skin folds.

All five patients with interdigital and dysidrotic forms of mycosis of the feet caused by *Trichophyton rubrum* who showed a similar clinical picture with maceration, exfoliation of the cutaneous horn as well as oedematous and hyperaemic skin and whose foot arch showed, against the background of oedematous and hyperaemic skin and hyperkeratosis, extensive abrasions with a bright-red bottom surrounded by fimbriated exfoliated epidermis, registered complete clinical recovery (with all results of ordinary and luminescent microscopy as well as of microbiological investigation being negative) after a 25-day course of treatment with a 0.5-percent ointment of the proposed preparation. The ointment was applied onto all affected areas once a day occlusively. The only residual manifestation was hyperkeratosis which had to be treated with keratolytics.

In all patients, after the first 3 or 4 days of treatment pronounced inflammatory manifestations disappeared and the abrasions and cracks started epithelizing, testifying to the antiphlogistic and reparative effect of the preparation.

All patients of this group had allergic rash on remote skin areas (leg, wrist, forearm) by the beginning of the course of treatment with the 0.5-percent ointment of the preparation; however, application of the preparation did nothing to intensify allergic manifestations or to give rise to para-allergic reactions in general.

One patient who suffered from diabetes mellitus was treated for interdigital candidosis (intertrigo blastomicetica). Daily application of the ointment of the preparation twice a day resulted in the disappearance of acute manifestations in the infection focus after 3 days of treatment and in complete clinical recovery (with the results of microbiological investigation being negative) after 10 days of treatment.

As for onychomycosis, the course of treatment using the ointment of the proposed preparation runs into months.

The proposed preparation was employed to treat onchomycosis of the fingers caused by *Trichophyton rubrum*, with seven nail-bodies being affected.

The clinical picture of mycosis of the end phalanxes of the fingers consisted of the afflictions of the nails and perinail-walls. The nail-bodies of the affected phalanxes of four fingers were totally destroyed; the nail matrices were uneven and thickened owing to the non-uniform pattern of hyperkeratosis. The horn squama were grayish-yellow. On the remaining three fingers, the nail-bodies were preserved but the edge zone was destroyed and serrated; subungual hyperkeratosis was in evidence.

The skin of the perinail-walls of all affected fingers were hyperaemic and infiltrated. Drops of pus oozed from under the nail-walls on pressing.

Subjectively, the patient complained of tension of the nail-wall skin and registered a painful reaction to palpation.

A 0.5-percent ointment of the preparation was applied once a day with an occlusive dressing following a medicated bath for the affected phalanxes containing a 1:10,000 solution of potassium manganate.

12 to 16 days after the beginning of the course of treatment, paronychia manifestations disappeared. The nails unmistakably started growing 3 to 4 weeks after the beginning of the specific course of treatment.

The course of treatment lasted 3 months. By the end of this period nail formation and complete clinical recovery, confirmed microscopically and microbiologically, were observed in four out of seven cases; in two cases onychomycosis manifestations persisted only about the free edge of the nails; in one case the treatment proved ineffective.

In the latter three cases where full recovery was not achieved, microbiological studies revealed cultures of yeast-like pathogenic fungi which had not been isolated previously while seeding the material from the affected areas.

In no cases was cutaneous application of the 0.5-percent ointment of the preparation (even over a long period of time) to humans accompanied by any side effect. Blood and urine tests of the patients subjected to the therapy in question confirmed the absence of any specific disorders. The preparation is easily tolerated by the patients and causes no skin irritation or allergic manifestations not only in healthy persons and mycosis patients, but also in patients suffering from eczema entailing considerable allergic transformations in the organism.

The proposed novel substances, viz. derivatives of dinitro-2,2'-bithiophene are preferably produced as follows.

The starting 5-substituted derivatives of 2,2'-bithiophene of the formula

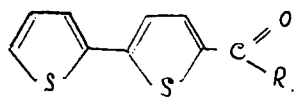

where
R = H or CH₃,
are nitrated at a low temperature with a nitrating mixture composed of concentrated nitric and sulfuric acids taken in the 1:2–2.5 ratio, with the derivatives of 2,2'-bithiophene subsequently recrystallized from appropriate organic solvents. The derivatives of dinitro-2,2'-bithiophene containing an azomethine group are obtained from dinitro-5-formyl-2,2'-bithiophene by condensing the latter with amino compounds followed by recrystallization. The yield of the desired product is up to 80 percent by weight.

The present invention will be further understood from the following examples illustrating the proposed novel substances, viz. derivatives of dinitro-2,2'-bithiophene, and the proposed process for the production thereof.

EXAMPLE 1

141.6 g of 5-acetyl-2,2'-bithiophene is dissolved at a temperature of from 0° to −5° C. in 1.416 ml of concentrated sulphuric acid of specific gravity 1.84, cooled down to −10°C., and admixed with a nitrating mixture made up of 62.8 ml of concentrated nitric acid of specific gravity 1.51 and 125.7 ml of concentrated sulfuric acid of specific gravity 1.84 and cooled down to −10°C. added dropwise, with the temperature being maintained in the range from −9° to −11°C. The reaction mixture is held in the cooling bath for 30 minutes, after which it is poured with stirring in a thin stream on chopped ice (seeing that no lumps are formed), the sediment is filtered off, washed with water to a neutral reaction and dried.

The nitrate is recrystallized from dioxane containing activated charcoal, 100 ml of dioxane being used up per 20 g of the product. The excess of dioxane is distilled off to give a first fraction (yield, 30 percent by weight) in the form of yellow crystals having a melting point of 121° to 122°C.; repeated recrystallization, from dioxane and then from heptane, gives 100 g of a pure end product (yield, 75 to 80 percent by weight), viz. 5',3'-dinitro-5-acetyl-2,2'-bithiophene, having a melting point of 122° to 122.5°C.

PMR spectrum: δH₄, 7.97 mln⁻¹; δH₄, 8.41 mln⁻¹; δH₃, 7.73 mln⁻¹; δCH₃, 2.78 mln⁻¹; δ₃,₄ = δ₄,₃ =5 Hz.

Analysis — Calc'd for $C_{10}H_6N_2O_5S_2$, wt.%: C, 40.26; H, 2.02; N, 9.38. Found, wt.%: C, 40.21; H, 2.18; N, 9.28.

The mother liquor additionally yields a second fraction of crystals having a melting point of 101° to 104°C. and then a third fraction of crystals having a melting point of 84° to 96°C. The second and third fractions (overall yield, 45 to 50 percent by weight) are constituted by a mixture of two isomers of dinitrobithiophene methylketone, namely: 5',3'-dinitro-5-acetyl-2,2'-bithiophene

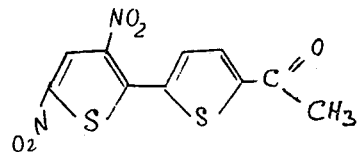

and 5',3-dinitro-5-acetyl-2,2'-bithiophene

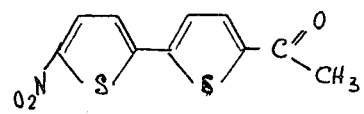

According to the PMR spectrum, the ratio of said isomers in the second fraction is 86.5 wt.% to 13.5 wt.%, while in the third fraction it is 51 wt.% to 49 wt.%, respectively.

Separation of said isomers is achieved by repeated recrystallization from isopropynol. In such a case, if the solution is cooled slowly, the 5',3'-dinitro-5-acetyl-2,2'-bithiophene isomer precipitates before the other isomer. Subsequently a certain amount of the second isomer is obtained from the mother liquor, viz. 5',3-dinitro-5-acetyl-2,2'-bithiophene, having a melting point of 136° to 136.5°C.; absorbing in the UV spectrum at $\lambda'_{max} = 280$ nm − $\epsilon'_{max} = 10,210$ and at $\lambda''_{max} = 376$ nm − $\epsilon''_{max} = 11,010$; and absorbing in the IR spectrum at νcm⁻¹: 1,663, 1,520, 1,412, 1,365, 1,332, 1,296, 1,262, 1,150, 1,040, 860, 802, 775, 745 and 723.

PMR spectrum: δH₄, 8.03 mln⁻¹; δH₄, 8.48 mln⁻¹; δH₃, 7.62 mln⁻¹; δCH₃, 2.81 mln⁻¹; δ₃',₄ = δ₄',₃' = 5 Hz.

Analysis — Calc'd for $C_{10}H_6N_2O_5S_2$, wt.%: C, 40.26; H, 2.02; N, 9.38. Found, Wt.%: C, 40.40; H, 2.12; N, 9.40.

EXAMPLE 2

158.4 g of 5'-nitro-5-formyl-2,2'-bithiophene is dissolved in 1,584 ml of concentrated sulfuric acid of specific gravity 1.84 at a temperature of 0°C. A nitrating mixture made up of 60.4 ml of concentrated nitric acid of specific gravity 1.348 and 148.5 ml of concentrated sulfuric acid of specific gravity 1.84 is added dropwise, with the temperature being maintained in the range 0° to −3°C. The reaction mixture is held with periodic stirring in a cooling bath for 30 minutes, after which it is poured on chopped ice, the sediment is filtered off, washed with water to a neutral reaction and dried.

The nitrate is recrystallized from a mixture made up of 1 part of benzene and 2 parts of hexane, additionally containing activated charcoal, to give 100 g of a product (43 percent by weight) which is constituted by a mixture of two isomers, namely: 5',3'-dinitro-5-formyl-2,2'-bithiophene

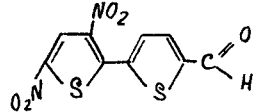

and 5',3-dinitro-5-formyl-2,2'-bithiophene

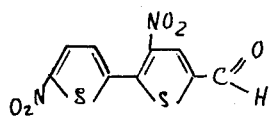

Said isomers are separated by repeated recrystallization.

Analysis — Calc'd for $C_9H_4N_2O_5S_2$, wt.%: C, 38.02; H, 1.41; N, 9.85. Found, wt.%: C, 38.14; H, 1.38; N, 9.97.

EXAMPLE 3

120 g of 5',3'-dinitro-5-formyl-2,2'-bithiophene is dissolved with heating in 6,000 ml of dry benzene, and 60 g of meta-aminobenzoic acid predissolved likewise in 6,000 ml of dry benzene is added. The reaction mixture is held for 2 hours in a boiling water bath, the excess of the solvent is distilled off, the precipitate formed on cooling is filtered off and recrystallized from alcohol.

The product is 100 g of -(5',3'-dinitro-2,2'-dithienylidene-5)-meta-aminobenzoic acid having the following empirical and structural formulas:

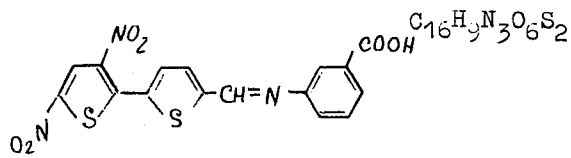

The product having a molecular weight of 403.38 is a reddish-orange, odorless, bitter crystalline powder, practically insoluble in water, scantily soluble in alcohol, lanolin and castor oil, soluble in dimethylformamide and dimethylsulfoxide, having a melting point of 195°C., sensitive to direct sunlight, but stable if stored in dark-glass vials.

Analysis — Calc'd for $C_{16}H_9N_3O_6S_2$, wt.%: N, 10.41. Found, wt.%; N, 10.56.

IR spectrum, cm$^{-1}$: $\nu$ C=O, 1,685; $\nu$ C=N' 1,614; $\nu$ NO$_2$, 1,520, 1.335.

What is claimed is:

1. A dinitro - 2,2'-bithiophene having the formula:

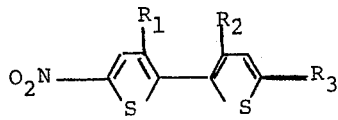

where $R_1$ is NO$_2$ when $R_2$ is H or $R_1$ is H when $R_2$ is NO$_2$; and $R_3$ is

—COCH$_3$ or

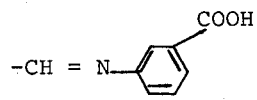

2. The dinitro -2,2'-bithiophene of claim 1 where $R_1$ is NO$_2$ $R_2$ is H and $R_3$ is —COCH$_3$.

3. The dinitro -2,2'-bithiophene of claim 1 where $R_1$ is H, $R_2$ is NO$_2$ and $R_3$ is —COCH$_3$.

4. The dinitro -2,2'-bithiophene of claim 1 where $R_3$ is

5. The dinitro -2,2'-bithiophene of claim 1 where R, is NO$_2$, $R_2$ is H and $R_3$ is

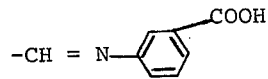

* * * * *